United States Patent
Stefan et al.

(10) Patent No.: US 10,217,298 B2
(45) Date of Patent: Feb. 26, 2019

(54) METHODS OF OPERATING A MOTOR VEHICLE

(71) Applicant: FORD GLOBAL TECHNOLOGIES, LLC, Dearborn, MI (US)

(72) Inventors: Frederic Stefan, Aachen (DE); Alain Marie Roger Chevalier, Henri-Chapelle (BE); Evangelos Bitsanis, Aachen (DE); Michael Marbaix, Haillot (BE)

(73) Assignee: Ford Global Technologies, LLC, Dearborn, MI (US)

( * ) Notice: Subject to any disclaimer, the term of this patent is extended or adjusted under 35 U.S.C. 154(b) by 58 days.

(21) Appl. No.: 15/498,092

(22) Filed: Apr. 26, 2017

(65) Prior Publication Data
US 2017/0316625 A1 Nov. 2, 2017

(30) Foreign Application Priority Data
Apr. 29, 2016 (DE) .......................... 10 2016 207 356

(51) Int. Cl.
| | |
|---|---|
| *G07C 5/08* | (2006.01) |
| *A61B 5/0205* | (2006.01) |
| *A61B 5/024* | (2006.01) |
| *A61B 5/053* | (2006.01) |
| *A61B 5/08* | (2006.01) |
| *A61B 5/11* | (2006.01) |
| *A61B 5/18* | (2006.01) |
| *G06F 3/16* | (2006.01) |

(Continued)

(52) U.S. Cl.
CPC ............ *G07C 5/0841* (2013.01); *A61B 5/024* (2013.01); *A61B 5/0205* (2013.01); *A61B 5/0531* (2013.01); *A61B 5/0816* (2013.01); *A61B 5/11* (2013.01); *A61B 5/165* (2013.01); *A61B 5/18* (2013.01); *A61B 5/6893* (2013.01); *A61B 5/749* (2013.01); *G06F 3/167* (2013.01); *G06N 5/04* (2013.01); *G06N 99/005* (2013.01); *G09B 7/02* (2013.01); *G09B 7/10* (2013.01); *G09B 19/16* (2013.01); *G09B 19/167* (2013.01); *A61B 3/112* (2013.01); *A61B 3/113* (2013.01); *A61B 2503/22* (2013.01); *G07C 5/008* (2013.01)

(58) Field of Classification Search
CPC .................................................. G07C 5/0841
See application file for complete search history.

(56) References Cited

U.S. PATENT DOCUMENTS

| | | |
|---|---|---|
| 6,571,191 B1 | 5/2003 | York et al. |
| 2002/0035429 A1 | 3/2002 | Banas |

(Continued)

OTHER PUBLICATIONS

William Strunk Jr. and E.B. White, The Elements of Style, 3rd Edition, all pages. (Year: 1979).*

*Primary Examiner* — Calvin Cheung
(74) *Attorney, Agent, or Firm* — Frank MacKenzie; Brooks Kushman P.C.

(57) ABSTRACT

A method of operating a motor vehicle includes detecting at least one motor vehicle driver response, producing a perception model based on the detected motor vehicle driver response, and analyzing the perception model to at avoid least one motor vehicle driver response by adjusting a parameter of the motor vehicle. Analysis of the perception model can also be carried out to predict a motor vehicle driver response, in particular during the generation of new control software for the vehicle.

9 Claims, 1 Drawing Sheet

(51) Int. Cl.
    *G06N 5/04*     (2006.01)
    *G06N 99/00*     (2010.01)
    *G09B 7/02*     (2006.01)
    *G09B 7/10*     (2006.01)
    *A61B 5/00*     (2006.01)
    *A61B 5/16*     (2006.01)
    *G09B 19/16*     (2006.01)
    *A61B 3/113*     (2006.01)
    *G07C 5/00*     (2006.01)
    *A61B 3/11*     (2006.01)

(56) References Cited

U.S. PATENT DOCUMENTS

| | | |
|---|---|---|
| 2006/0047381 A1 | 3/2006 | Nguyen |
| 2011/0213511 A1 | 9/2011 | Visconti |
| 2012/0303392 A1 | 11/2012 | Depura |

\* cited by examiner

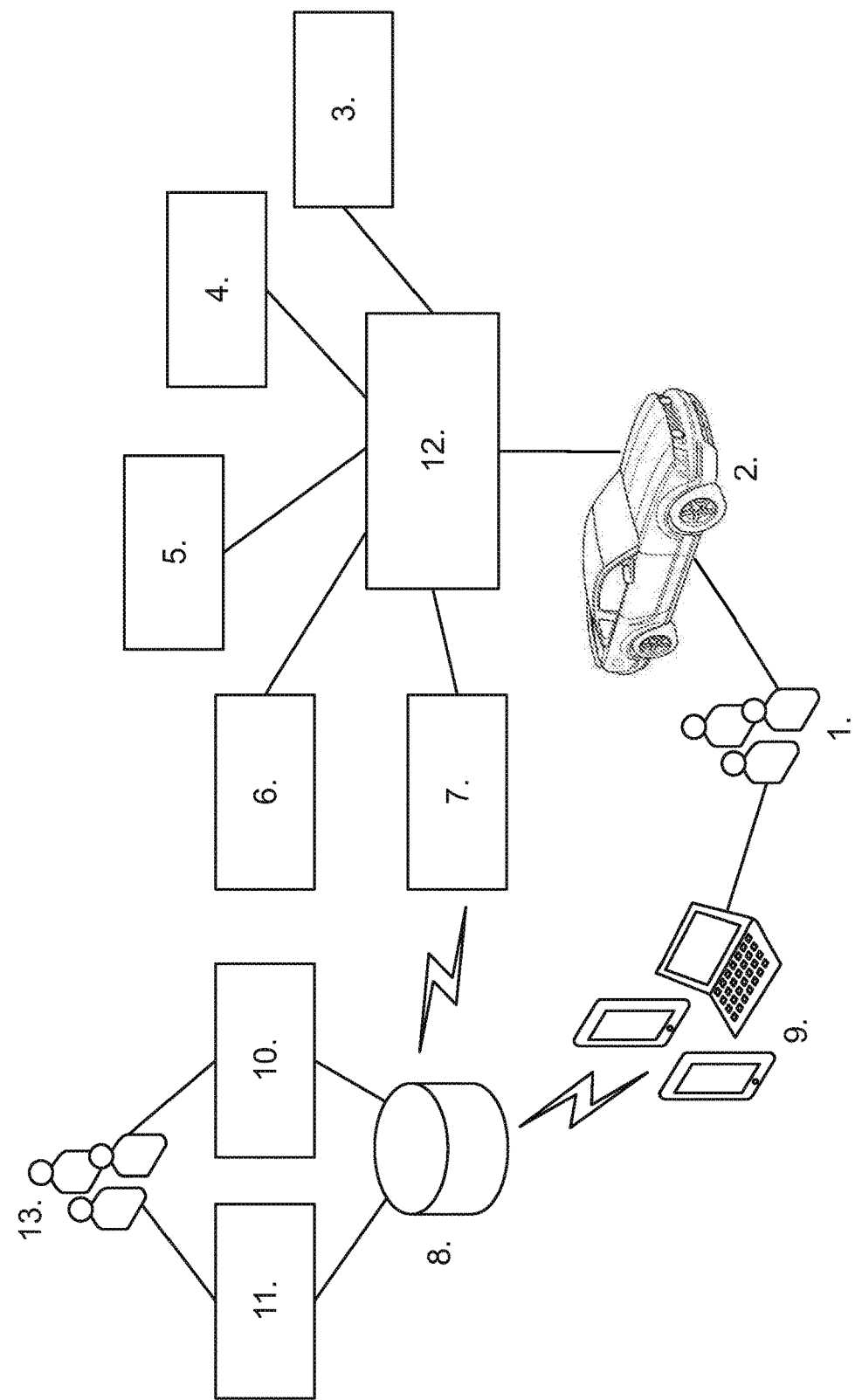

METHODS OF OPERATING A MOTOR VEHICLE

CROSS-REFERENCE TO RELATED APPLICATIONS

This application claims foreign priority benefits under 35 U.S.C. § 119(a)-(d) to DE Application 10 2016 207 356.7 filed Apr. 29, 2016, which is hereby incorporated by reference in its entirety.

TECHNICAL FIELD

The disclosure concerns a method of operating a motor vehicle.

BACKGROUND

Motor vehicle drivers have different expectations regarding the driving behavior of their motor vehicle. Driver expectations can depend on a use of the motor vehicle, on a personality, a sensitivity or an experience of the driver of the motor vehicle.

A primary expectation of motor vehicle drivers concerns, for example, fuel consumption and harmful emissions. Also, some motor vehicle drivers prefer a rather conservative driving style, whereas others prefer a sporty manner of driving.

Some motor vehicle drivers regard their motor vehicles as a means of transport in urban traffic at comparatively low speeds, while others drive on freeways at high speeds. Finally, some motor vehicle drivers are interested in sporty driving of the motor vehicle.

Finally, some motor vehicle drivers are more sensitive to noise, vibrations and acceleration response than others.

Because the perception of motor vehicle drivers is highly subjective, it is very difficult to adjust the behavior of software and calibrations so that they meet the expectations of all motor vehicle drivers.

SUMMARY

The object of the disclosure is achieved by a method of operating a motor vehicle, with the steps:

Detecting at least one motor vehicle driver response,

Producing a perception model based on the detected motor vehicle driver response, and Analyzing the perception model in order to avoid at least one motor vehicle driver response by adjusting a parameter of the motor vehicle.

The perception model simulates the responses of motor vehicle drivers occurring during the operation of motor vehicles using neural networks, fuzzy logic or other techniques of artificial intelligence (AI). The perception model also enables the determination of when motor vehicle drivers tend towards startled reactions, such as, for example, because of an unexpected acceleration, by running simulations of various driving situations and subsequent automatic analysis, for example by cluster formation. Suitable adjustment of motor vehicle parameters counteracts the occurrence of corresponding driving situations.

According to one embodiment, motor vehicle state parameters are detected and associated with the detected responses of the motor vehicle driver. The motor vehicle parameters may include the speed of the motor vehicle, the revolution rate of the engine or the acceleration or braking.

According to a further embodiment, motor vehicle sensor values are detected and associated with the detected responses of the motor vehicle driver. The motor vehicle sensor values may include a motor vehicle position, a traffic situation with other road users or traffic signals.

According to a further embodiment, the detected motor vehicle driver response is classified as a positive and/or negative response of the driver. The detected motor vehicle driver response may include measurement values of the pupil size, the pitch of the voice, the heart rate, the breathing rate, the body movement, the eye movement or the skin resistance of the driver of the motor vehicle.

According to a further embodiment, at least one motor vehicle driver input is taken into account when producing the perception model. Thus, not only are measurement values detected with sensors, but also the subjective perception of motor vehicle drivers can be taken into account. For example, a motor vehicle driver input can be carried out by means of a location-independent software module. The software module can comprise voice recognition or is menu-driven.

According to a further embodiment, the perception model is designed to predict a motor vehicle driver response. In particular, if a new version of motor vehicle control software is produced, the resulting response of the driver of the motor vehicle can be predicted. This enables the developer to get an indication of how motor vehicle control software can be developed that meets the expectations of the driver of the motor vehicle.

The disclosure further comprises a computer program product and a motor vehicle, each designed to implement such a method.

BRIEF DESCRIPTION OF THE DRAWINGS

The FIGURE shows a schematic representation of a system for producing a perception model.

DETAILED DESCRIPTION

As required, detailed embodiments of the present disclosure are disclosed herein; however, it is to be understood that the disclosed embodiments are merely exemplary of the disclosure that may be embodied in various and alternative forms. The FIGURES are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present disclosure.

A motor vehicle 2 is represented with control software 12 that controls various functions of the motor vehicle 2, such as, for example, the response of an engine, operation of a gas pedal and/or brakes, operation of a brake pedal, a steering behavior or a gear change in the case of an automatic gearbox. The control software 12 comprises variable parameters for this purpose.

Furthermore, in the present exemplary embodiment, the motor vehicle 2 comprises a driver response observation module 3. During the operation of the motor vehicle 2, using suitable sensors, the driver response observation module 3 detects pupil size, pitch of the voice, heart rate, breathing rate, body movement, eye movement and/or skin resistance of a driver of the motor vehicle 1, and combines the variables into driver response data.

Furthermore, in the present exemplary embodiment, the motor vehicle 2 comprises a driving state observation module 4. The driving state observation module 4 detects motor vehicle state parameters, such as speed of the motor vehicle, revolution rate of the engine, or acceleration or braking and/or motor vehicle sensor values, such as, for example, a motor vehicle position, a traffic situation with other road users or traffic signals, and combines said variables into driving state data.

Moreover, in the present exemplary embodiment the motor vehicle 2 comprises a motor vehicle response observation module 5. The motor vehicle response observation module 5 detects the motor vehicle behavior, and analyzes the behavior in order to detect patterns by cluster formation, such as, for example, acceleration patterns, impulse patterns, motor vehicle speed patterns, a noise level and/or a vibration level, and combines the variables into motor vehicle response data.

A classifying module 6 is associated with the motor vehicle 2. The classifying module 6 is designed to read the driver response data detected by the driver response observation module 3, and to classify the driver response data as positive or negative responses of the driver of the motor vehicle 1. For example, an increase in measurement values of pupil size, pitch of the voice, heart rate, breathing rate, body movement, eye movement and/or skin resistance are viewed as stress symptoms of the driver of the motor vehicle 1, and are, therefore, classified as negative responses. On the other hand, other responses can be classified as positive responses.

Furthermore, in the present exemplary embodiment the classifying module 6 is designed to read in the driving state data detected by the driving state observation module 4 and the motor vehicle response data detected by the motor vehicle response observation module 5, and assign respective classified responses in order to be able to assign measurement values to negative responses, for example.

Furthermore, in the present exemplary embodiment an input module 7 is associated with the motor vehicle 2. The input module 7 enables the direct input of subjective impressions of the driver of the motor vehicle 1, and the transmission of the subjective impressions to a central server, for example, by means of wireless data transmission. The input module 7 can for example be designed to prompt the motor vehicle driver 1 after the end of each journey to answer questions. The questions can be answered in a natural language and the input module 7 comprises speech recognition. Alternatively, the responses can be entered directly into windows of a menu, for example as numerical inputs in the form of 3 of 5 points, for example. With the agreement of the driver of the motor vehicle 1, the responses are transmitted to the server.

A database 8 with which the incoming data as well as the classified responses with the assigned data from the classifying module 6 are collected runs on the server.

Besides the input module 7, the motor vehicle driver can also make entries into the database 8 via an interface 9 to the database 8. The inputs can be independent of a menu and can thus be freely formulated, and can further be made at any time and from any location, i.e. not only immediately after a journey.

A software parameter optimizing module 10 has access to the data of the database 8. The software parameter optimizing module 10 analyzes the data, for example for negative responses, produces a perception model of motor vehicle drivers 1, for example based on neural networks or fuzzy logic, and thus enables a development team 13 to investigate the consequences of changes of parameters. Furthermore, it can be investigated in an automatic manner how changes of parameters affect the frequency of negative responses, and a new set of parameters is determined using a quality criterion that weights the various negative responses differently.

Furthermore, a design module 11 has access to the data of the database 8. For example, new driving situations for which an adjustment of software that goes beyond the adjustment of parameters is necessary can be determined by the development team 13 or by algorithms, for example for the classification of data or for example in order to estimate how drivers would react to software changes.

The driver response observation module 3, the driving state observation module 4, the motor vehicle response observation module 5, the classifying module 6, the input module 7, the database 8, the interface 9, the software parameter optimizing module 10, the software design module 11 and the control software 12 can comprise hardware components and/or software components for this purpose.

During operation, the driver response observation module 3 detects pupil size, pitch of the voice, heart rate, breathing rate, body movement, eye movement and/or skin resistance of a driver of the motor vehicle 1, and combines the variables into driver response data.

Furthermore, the driving state observation module 4 detects motor vehicle state parameters, such as speed of the motor vehicle, revolution rate of an engine, or acceleration or braking and/or motor vehicle sensor values, such as for example a motor vehicle position, a traffic situation with other road users or traffic signals, and combines the variables into driving state data.

Furthermore, the motor vehicle response observation module 5 detects the motor vehicle behavior, and analyzes the behavior in order to detect patterns by cluster formation, such as, for example, acceleration patterns, impulse patterns, motor vehicle speed patterns, a noise level and/or a vibration level, and combines the variables into motor vehicle response data.

The classifying module 6 reads in the detected driver response data, and classifies the driver response data as positive or negative responses of the driver of the motor vehicle 1.

Furthermore, the classifying module 6 reads in the driving state data and the motor vehicle response data, and assigns the driving state and motor vehicle data to the respective classified responses.

At the end of a journey, the motor vehicle driver 1 can make inputs with the input module 7 that are transmitted to the server with the agreement of the driver of the motor vehicle 1. Alternatively, the motor vehicle driver can also make inputs directly via the interface 9 to the database inputs.

The software parameter optimizing module 10 analyzes the data for negative responses, and produces a perception model of motor vehicle drivers 1, whereas with the software design module 11 new driving situations for which an adjustment of software that goes beyond the adjustment of parameters is necessary can be determined.

The occurrence of corresponding driving situations can thus be counteracted by a suitable adjustment of motor vehicle parameters.

While exemplary embodiments are described above, it is not intended that these embodiments describe all possible forms of the disclosure. Rather, the words used in the specification are words of description rather than limitation, and it is understood that various changes may be made without departing from the spirit and scope of the disclosure.

Additionally, the features of various implementing embodiments may be combined to form further embodiments of the disclosure.

What is claimed is:

1. A method of operating a motor vehicle comprising:
   detecting a negative driver response to a vehicle state parameter;
   producing a perception model correlating the negative driver response with the vehicle state parameter;
   analyzing the perception model; and
   adjusting a parameter of a motor vehicle function to avoid future occurrences of driving situations that, based on the analysis of the perception model, would cause a second negative driver response.

2. The method as claimed in claim 1 further comprising:
   detecting motor vehicle sensor values; and
   assigning the motor vehicle sensor values to the driver response for use in the production of the perception model.

3. The method as claimed in claim 1, wherein producing the perception model further takes into account at least one motor vehicle driver input.

4. The method as claimed in claim 1, wherein the perception model is configured to predict a motor vehicle driver response.

5. A system for adjusting vehicle functions comprising:
   a vehicle having a plurality of sensors configured to detect, during operation of the vehicle, values indicating a driver response, a vehicle driving state, and a vehicle response, and the vehicle further having control software configured to control operation of a plurality of vehicle systems;
   a classifying module configured to classify the values indicative of a driver response as at least one of a positive response and a negative response, and to assign the driving state values and vehicle response values to at least one of the respective positive and negative response classifications; and
   an optimizing module configured to produce a driver perception model from the classified data, to use the driver perception model to simulate driver responses during future vehicle operation, and to cause adjustments to the control software necessary to avoid further driver negative responses.

6. The system as claimed in claim 5, wherein data indicative of the driver response includes pupil size, vocal pitch, heart rate, breathing rate, body movement, eye movement and skin resistance of a driver.

7. The system as claimed in claim 5, wherein data indicative of the driving state includes vehicle state parameters and vehicle sensor values.

8. The system as claimed in claim 5, wherein data indicative of the vehicle response observation includes analysis of vehicle behavior to detect patterns by cluster formation.

9. The system as claimed in claim 5 further comprising an interface connected to the input module, wherein a driver provides the direct input to the input module via the interface.

* * * * *